United States Patent [19]
Blakeley et al.

[11] Patent Number: 5,323,776
[45] Date of Patent: Jun. 28, 1994

[54] MRI COMPATIBLE PULSE OXIMETRY SYSTEM

[75] Inventors: Douglas M. Blakeley, Euclid; Robert C. Gauss, Aurora; David C. Flugan, Richmond Hts., all of Ohio

[73] Assignee: Picker International, Inc., Highland Hts., Ohio

[21] Appl. No.: 961,150

[22] Filed: Oct. 15, 1992

[51] Int. Cl.$^5$ ............... A61B 5/0245; A61B 5/055
[52] U.S. Cl. .................... 128/633; 128/653.2; 128/653.5; 128/666; 128/687; 128/901
[58] Field of Search ............. 128/633, 653.2, 653.5, 128/666, 901, 687

[56] References Cited

U.S. PATENT DOCUMENTS

| | | | |
|---|---|---|---|
| 4,545,384 | 10/1985 | Kawachi | 128/653 |
| 4,763,075 | 1/1988 | Weigert | 324/318 |
| 4,991,580 | 2/1991 | Moore | 128/653.5 |
| 4,991,587 | 2/1991 | Blakeley et al. | 128/653 |
| 5,159,929 | 11/1992 | Morris et al. | 128/653.2 |

FOREIGN PATENT DOCUMENTS

0132785A3 2/1985 European Pat. Off. .

OTHER PUBLICATIONS

"Monitoring of Acutely Ill Patients During Nuclear Magnetic Resonance Imaging: Use of a Time-Varying Filter Electrocardiographic Gating Device to Reduce Gradient Artifacts", Rokey, et al. Magnetic Resonance in Medicine 6, 240–245 (1989) pp. 240–245.

*Primary Examiner*—Ruth S. Smith
*Attorney, Agent, or Firm*—Fay, Sharpe, Beall, Fagan, Minnich & McKee

[57] ABSTRACT

Magnetic resonance imaging hardware (A) defines a patient receiving region (20) that is surrounded by a bore liner (22). A socket (50) is mounted in the bore liner with an appropriate receptacle for receiving a standard plug (52) of a conventional pulse oximetry system. Conventional pulse oximetry systems include a sensor unit (54) connected with a cable (56) having the plug (52) at one end thereof. A notch filter (62) attenuates currents near the resonance frequency of the imager. A preamplifier (60) amplifies signals from the sensor unit. Within the shielding (66) of the preamplifier, a low pass filter (68) is provided to remove induced radio frequency components from the preamplified sensor unit signal. A radio frequency filter (70) mounted at the shield of the shielded room (B) prevents radio frequency signals from reaching an exterior processing and display unit (E) and prevents radio frequency signals from a clock (72) of the processing and display unit from being conveyed into the shielded room (B). The processing and display unit processes the signal received from the preamplifier to generate a pulse rate display (78) and a blood oxygen concentration display (80).

20 Claims, 2 Drawing Sheets

MRI COMPATIBLE PULSE OXIMETRY SYSTEM

BACKGROUND OF THE INVENTION

The present application is directed to the art of monitoring physiological conditions within a high magnetic field environment. The present invention finds particular application in conjunction with pulse oximetry measurements within the bore of a magnetic resonance imaging apparatus and will be described with particular reference thereto. It is to be appreciated, however, that the invention will also find application in conjunction with the measurement of other physiological conditions within MRI equipment or other equipment with strong, changing, magnetic fields.

During a diagnostic examination, physicians often want to monitor various physiological conditions. Among these conditions are the patient's pulse rate and blood oxygen content. Pulse oximetry equipment is commonly available off-the-shelf for measuring a patient's pulse and blood oxygen content. Typically, a pulse oximetry system includes a visible red and an infrared light source, such as a pair of light emitting diodes. The light sources and a light sensor are mounted in a sensor unit that is attached to the patient such that the light passes through a portion of the patient before reaching the light sensor. The amount of blood oxygen is readily determinable from the difference in the absorption of these two wavelengths of light.

Typically, a cable extends from the sensor unit to a processing and display unit. The processing and display unit provides electrical power along the cable for the light emitting diodes and the sensor. This unit further receives signals from the sensor and performs an appropriate analysis to determine the patient's blood oxygen content and pulse rate.

It has been proposed to clip the pulse oximeter sensor unit to a patient before placement in the bore of a magnetic resonance imager and position the processing and display unit adjacent the exterior of the bore where its display can be viewed by the doctor or attendant. However, this has several drawbacks. First, the processing and display units typically have an internal clock, e.g. a microprocessor clock, which has harmonics at or near the resonance frequencies of a magnetic resonance imager. An 0.5 Tesla MRI machine has about a 21 MHz resonance frequency; a 1.0 Tesla MRI machine has about a 42 MHz resonance frequency; and a 1.5 Tesla MRI machine has about a 64 MHz resonance frequency. The processing and display unit and the lead running to the sensor unit tend to broadcast radio frequency signals of the microprocessor clock frequency and its harmonics into the bore of the magnetic resonance imaging apparatus. These radio frequency signals interfere with the proper operation of the magnetic resonance imager, degrading the resultant images.

Second, the electrical leads extending from the processor and display unit to the sensor unit act as the secondary or pick-up coil when subject to the changing magnetic fields of the magnetic resonance imager. That is, the changing magnetic fields in the bore tend to induce like currents in the electrical leads extending between the sensor unit and the processing and display unit. These radio frequency currents in the lead can interfere with the proper processing of the pulse oximetry signals and even damage the processor and display unit. Yet more dangerous, these same induced RF currents can cause excessive electrical inductive and resistance heating, particularly adjacent the sensor unit. This can cause RF burns on the patient.

With these problems in mind, others have produced a pulse oximetry unit in which the sensor unit is connected with the processor and display unit by fiber optic cables. Because there are no electrical cables extending through the magnetic resonance imager bore, there is no possibility of RF burns to the patient or RF induced noise in the signal conveyed to the processor and display unit. However, the fiber optic leads tend to be relatively delicate and easily broken. Once damaged, the cost of repair is very high. Further, the fiber optic systems normally require different clips for patients of different size, particularly separate adult and pediatric clips or sensor units. Individual sensor units are again very expensive.

Another solution is to encase the sensor unit in a shielded mit. The mit and the cable are surrounded with a grounded shield. This system prevents RF currents from being induced on the conductors connecting the sensor unit with the processing and display unit, eliminating the interference which such RF currents can cause with both the signals coming to the processing unit and the signals going to the sensing unit. However, the RF magnetic fields can induce RF currents in the shielding which RF currents can still cause RF burns to the patient.

The present invention provides a new and improved combination MRI imaging apparatus and pulse oximetry system which overcomes the above-referenced problems and others.

SUMMARY OF THE INVENTION

In accordance with a first aspect of the present invention, a magnetic resonance imaging apparatus is disposed within a shielded room. A pulse oximetry system is provided which has a processing and display unit disposed exterior of the room. A pick up or sensor unit is disposed within the bore of the magnetic resonance imaging system in connection with the patient. A preamplifier is connected electrically between the sensor unit and the processing and display unit. At the wall of the shielded room, a filter is provided for isolating the processing and display unit from a magnetic resonance imaging apparatus. In particular, the filter prevents clock harmonics which approximate the resonance frequency of the magnetic resonance imaging apparatus from entering the shielded room.

In accordance with a second aspect of the present invention, the preamplifier is mounted, shielded and grounded directly to the magnet of the magnetic resonance imaging apparatus.

In accordance with another aspect of the present invention, a low pass filter is connected with the grounded preamplifier within its shielding. The low pass filter blocks the flow of radio frequency signals from the cables and the sensor unit back to the processing and display unit. In this manner, RF interference is blocked from interfering with the signals processed by the processing and display unit.

In accordance with another aspect of the present invention, a notch filter is provided between the preamplifier and the sensor unit. The notch filter blocks the passage of RF signals in a range closely proximate to the resonance frequency. This inhibits RF induced currents from flowing through the cabling and causing RF burns to the patient.

In accordance with another aspect of the present invention, the preamplifier is mounted on an exterior of the magnet. Wiring runs through the magnet housing and is connected to a socket mounted in a bore liner of the magnetic resonance imager. The socket has a standard configuration for existing pulse oximetry equipment. A sensor unit and lead combination can be plugged into the socket and used in the MRI equipment or used anywhere else in the hospital with other compatible pulse oximetry equipment that the hospital or clinic may have.

One advantage of the present invention is that it eliminates harmonic interference from the clock of a pulse oximetry unit with MRI imaging techniques.

Another advantage of the present invention is that it inhibits RF burning of the patient.

Another advantage of the present invention is that it is compatible with standard and existing pulse oximeter equipment. No modifications are necessary to the sensor unit or the peripheral equipment, enabling the hospital or clinic to use the same pulse oximetry equipment in the MRI room that they use in other areas of the hospital or clinic.

Still further advantages of the present invention will become apparent to those of ordinary skill in the art upon reading and understanding the following detailed description of the preferred embodiment.

BRIEF DESCRIPTION OF THE DRAWINGS

The invention may take form in various components and arrangements of components and in various steps and arrangements of steps. The drawings are only for purposes of illustrating a preferred embodiment and are not to be construed as limiting the invention.

DETAILED DESCRIPTION OF THE PREFERRED EMBODIMENT

Figure 1:
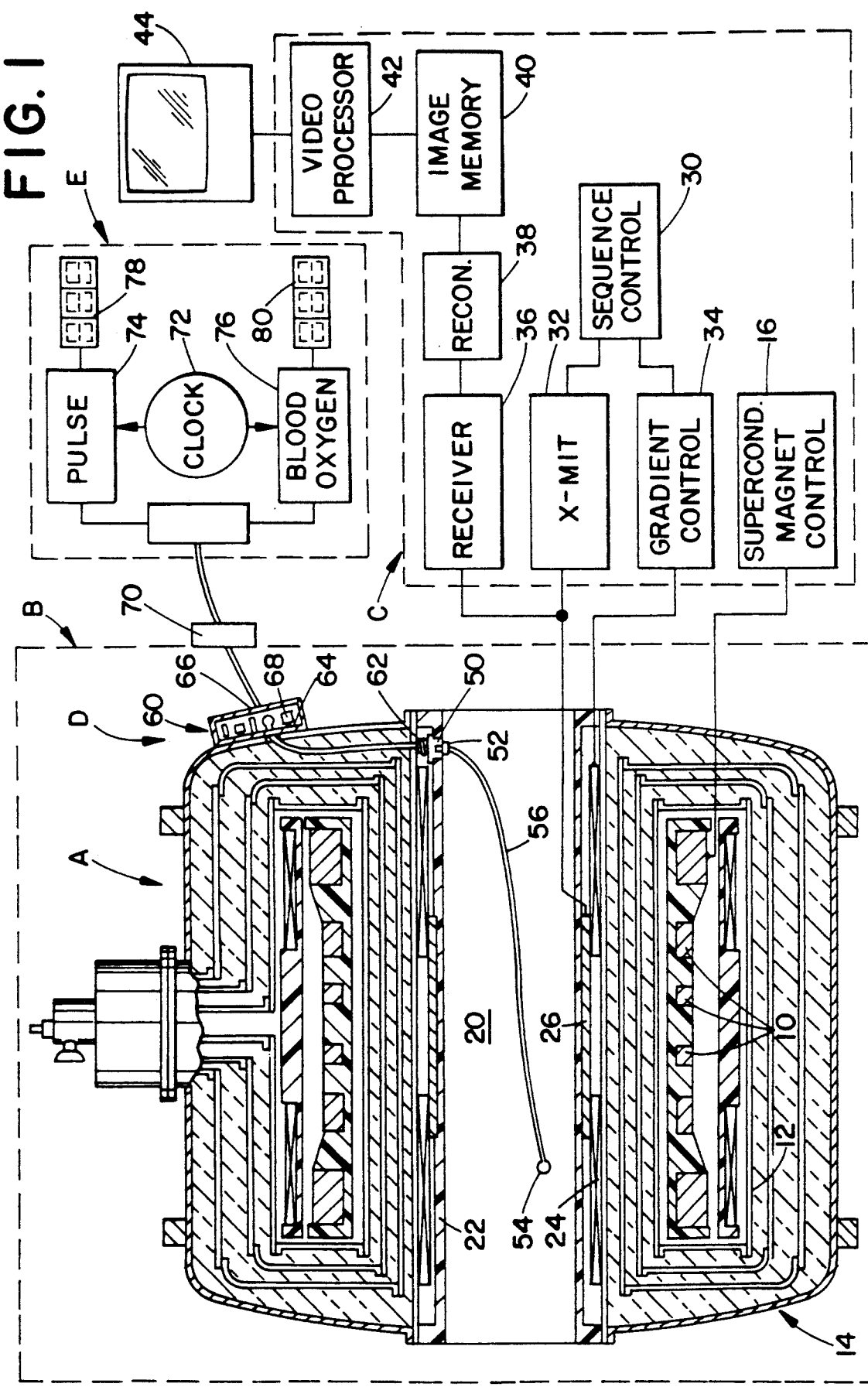
FIG. 1 is a diagrammatic illustration of a magnetic resonance imaging apparatus and pulse oximetry system in accordance with the present invention; and, FIG. 2 is a diagrammatic illustration of the pulse oximetry system in accordance with the present invention.

A magnetic resonance imaging apparatus A is disposed within a shielded room B. An electronic control and processing portion C of the magnetic resonance equipment is disposed exterior to the shielded room. A pulse oximetry system includes a first, in-field portion D disposed within the shielded room B and a processing and display portion E disposed exterior to the shielded room B.

More specifically to the preferred embodiment, the magnetic resonance imaging hardware A includes a superconducting magnet 10 which is contained in a helium reservoir 12. A series of vacuum dewars 14 surround the helium reservoir 12 to assist in maintaining the superconducting magnet 10 at superconducting temperatures. Preferably, additional refrigeration unit (not shown) are provided for removing heat from the vacuum dewars to reduce helium boil-off from the helium reservoir 12. A superconducting magnetic control circuit 16 provides appropriate controls to ramp up the superconducting magnet and provide any additional electronic controls which might be necessary. Preferably, a helium recovery system is provided for recovering and re-liquefying helium which is boiled-off to maintain the superconducting magnetic in its superconducting state.

The superconducting magnet 10 maintains a substantially uniform magnetic field longitudinally through a patient receiving central bore 20 of the magnetic resonance imaging hardware. The bore is lined with a bore liner 22 which protects x, y, and z-gradient coils 24 and a radio frequency receiver and transmitter coil 26 from damage. A patient couch (not shown) is conventionally provided for facilitating ingress and egress of the patient from the central bore 20.

The magnetic resonance control unit C includes a sequence control unit 30 which causes a digital radio frequency transmitter 32 and a gradient control 34 to apply appropriate RF signals to the RF coil 26 and gradient current pulses to the gradient coils 24 to implement a preselected imaging sequence. The gradient and radio frequency pulses induce and manipulate magnetic resonance causing resonating dipoles within the bore 20 to generate magnetic resonance signals which are received by a digital radio frequency receiver 36. An image reconstruction processor 38 processes the received magnetic resonance signals into an electronic image representation which is stored in an image memory 40. A video processor 42 converts electronic image representations from the image memory 40 into the appropriate format for display on a video monitor 44.

Figure 2:
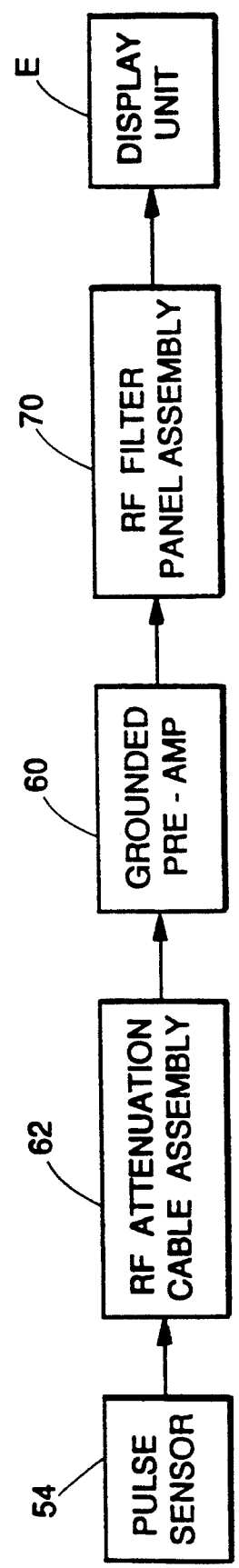

With continuing reference to FIG. 1 and further reference to FIG. 2, the internal pulse oximeter portion D includes a socket 50 mounted flush or recessed in the bore liner 22. The socket is disposed near the upper portion of the bore liner where it does not interfere with or become obscured by the patient couch or the patient. Preferably, the socket 50 is disposed adjacent one end of the bore to facilitate access by the operator for plugging in the plug end 52 of a conventional pulse oximeter sensor unit 54 with attached cable 56. The sensor unit, conventionally includes light emitting diodes for generating visible red and infrared light and a light pick-up for receiving light from the red and infrared light sources which has traversed a thin portion of the patient. Again, the lead 56 and sensor unit 54 are the same lead and sensor portion as are used with this oximetry system in other areas of the hospital or clinic facility.

A preamplifier 60 is mounted directly on the dewar and magnet assembly for amplifying signals from the sensor unit. A notch filter 62 presents a high impedance to radio frequency currents with a frequency near the resonance frequency of the MRI apparatus A. For a 1.5 Tesla magnet in which the resonance frequency is about 64 MHz, the notch filter 62 presents a high impedance to currents near the 64 MHz resonance frequency range, e.g. currents in the 60–68 MHz range. This high impedance rapidly attenuates any RF currents induced in the lead 56 by the RF pulses. In the preferred embodiment, the notch filter is constructed of a lead material similar to lead 56 which is wound about a dozen times around a plastic former. The frequency of the filter is adjusted by wrapping or unwrapping the cable by a partial turn or so around the plastic former.

The preamplifier 60 has a ground layer 64 which is connected with the dewars of the superconducting magnet assembly and is surrounded by a shield 66. Within the shield 66 are contained the various amplification components of the preamplifier as well as a low pass filter 68 to prevent RF signals from being superimposed on the electrical signals from the pulse sensor unit 54.

A radio frequency filter 70 is mounted on an electrically conductive shielding surface which lines the shielded room B to prevent any RF signals superimposed on the cabling leading from the preamplifier to the shielded room wall from passing to the exterior pulse oximeter portion E and to prevent any harmonics of the clocking signal from the processing and display unit E from being conveyed into the shielded room. The processing and display unit E includes a clock 72 which controls the digital processing of the received signals by a pulse detector 74 and a blood oxygen concentration analyzer 76. The pulse detector 74 determines the patient's pulse which is displayed on an appropriate digital display 78. The blood oxygen concentration analyzer 76 controls a digital display 80 which displays the current blood oxygen concentration.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A combined magnetic resonance imaging and pulse oximetry system comprising:
   a bore liner for defining a patient receiving region;
   a magnet assembly for generating a strong, substantially uniform magnetic field through the patient receiving region, the magnet assembly being mounted adjacent the bore liner;
   a gradient coil assembly for inducing magnetic field gradients across the magnetic field, the gradient coil assembly being mounted between the magnet assembly and the bore liner;
   an RF coil means for transmitting and receiving radio frequency signals into and from the patient receiving region, the RF coil means including a coil mounted between the gradient coil assembly and the bore liner;
   a gradient control means for controlling the gradient coil assembly, the gradient control means being connected with the gradient coil assembly;
   a radio frequency transmitter for controlling transmission of radio frequency signals by the RF coil means, the radio frequency transmitter being connected with the RF coil means;
   a receiver means for receiving magnetic resonance signals from the patient receiving region, the receiver means being connected with the radio frequency coil means;
   a reconstruction means for reconstructing magnetic resonance signals received by the radio frequency receiver into a digital image representation, the reconstruction means being connected with the receiver means;
   a pulse oximetry sensor unit;
   an electrical lead connected with the pulse oximetry sensor unit;
   a socket mounted in the bore liner detachably receiving a plug on an end of the electrical lead connected with the pulse oximetry sensor unit;
   a preamplifier connected with the socket for amplifying electrical signals from the sensor unit;
   a processing and display means connected with the preamplifier for processing electrical signals therefrom to generate a display of at least patient blood oxygen concentration.

2. The apparatus as set forth in claim 1 further including a filter means disposed between the socket and the preamplifier for blocking the passage of resonance frequency signals.

3. The apparatus as set forth in claim 1 wherein the preamplifier is grounded to the magnet assembly and surrounded by a shield connected with the magnet assembly.

4. The apparatus as set forth in claim 3 including a low pass filter mounted inside the shield with the preamplifier for preventing radio frequency signals from being superimposed on the electrical signals from the sensor unit.

5. The apparatus as set forth in claim 1 wherein the bore liner, the socket, the magnet assembly, the gradient coils, the RF coil means, and the preamplifier are disposed within a shielded room which is surrounded by an electrically conductive shielding surface and further including:
   a radio frequency filter means connected between the preamplifier and the processing and display means and connected with the shielding surface to (i) prevent the passage of radio frequency signals from the preamplifier to the processing and display means and (ii) prevent the passage of radio frequency signals from the processing and display means into the shielded room.

6. The apparatus as set forth in claim 5 wherein the processing and display means includes a clock generator which generates a radio frequency signal, the resonance frequency and the radio frequency signal being harmonics of each other.

7. The apparatus as set forth in claim 1 wherein:
   the sensor unit includes means for sensing characteristics of a patient's blood such that the electrical signals from the sensor unit are indicative of the sensed characteristics of the patient's blood, an electrical power supply, the electrical lead connected with the electrical power supply to supply electrical power to the sensor unit, the preamplifier amplifies the electrical signals indicative of the blood characteristics, and the processing and display means processes electrical signals indicative of the blood characteristics from the preamplifier such that the generated display is a display of pulse and blood oxygen concentration, the processing and display means includes a radio frequency clock, and further including:
   a filter means disposed between the sensor unit and the preamplifier for presenting a high impedance to radio frequency signals in a selected frequency range;
   a radio frequency filter disposed between the preamplifier and the processing and display means for preventing radio frequency clock signals from the radio frequency clock from being conveyed to the preamplifier and for preventing radio frequency signals from being conveyed from the preamplifier to the processing and display means.

8. A pulse oximeter apparatus in conjunction with a magnetic resonance apparatus disposed in a shielded room, the magnetic resonance imaging apparatus including:
   a bore liner which defines a patient receiving region;
   a vacuum dewar connected with the bore liner;
   a magnet assembly disposed in the vacuum dewar for generating magnetic fields through the patient receiving region;

an RF coil means disposed adjacent the bore liner for transmitting and receiving radio frequency signals into and from the patient receiving region;

the pulse oximeter apparatus comprising:

a pulse oximetry sensor unit with an electrical lead disposed in the bore liner;

a preamplifier grounded to the vacuum dewar and surrounded by a shield connected with the vacuum dewar, the preamplifier being connected with the sensor unit lead for amplifying electrical signals from the sensor unit;

a processing and display means disposed exterior to the shielded room and connected with the preamplifier for processing electrical signals therefrom to generate a display of at least patient pulse and blood oxygen concentration.

9. A pulse oximetry apparatus comprising:

a sensor unit means for sensing characteristics of a patient's blood;

an electrical lead connected with the sensor unit means for supplying electrical power thereto and conveying electrical signals indicative of the blood characteristics;

an electrical plug connected with the lead;

an electrical socket releasably interconnected with the plug, the socket being adapted for mounting within a patient receiving bore of a magnetic resonance apparatus;

a preamplifier connected with the socket for amplifying the electrical signals indicative of the blood characteristics;

a filter means disposed between the sensor unit means and the preamplifier for presenting a high impedance to radio frequency signals in a selected range;

a processing and display means for processing the electrical signals indicative of the blood characteristics from the preamplifier to derive a display of pulse and blood oxygen concentration of a patient who is sensed by the sensing unit means, the processing and display means including a radio frequency clock;

a radio frequency filter disposed between the preamplifier and the processing and display means for preventing radio frequency signals from the clock from being conveyed to the preamplifier and for preventing radio frequency signals from being conveyed from the preamplifier to the processing and display means.

10. The apparatus as set forth in claim 9 wherein the preamplifier is housed in a grounded shield and further including a low pass filter within the shield.

11. The apparatus as set forth in claim 9 further including a notch filter constructed of a section of the lead wrapped in a coil arrangement, the notch filter being disposed between the socket and the preamplifier.

12. A magnetic resonance imaging apparatus comprising:

a bore liner which defines a patient receiving region therein;

a magnet assembly for generating a strong, substantially uniform magnetic field through the patient receiving region defined within the bore liner;

a gradient coil assembly disposed adjacent the patient receiving region for inducing magnetic field gradients across the magnetic field;

an RF coil means for transmitting radio frequency signals into and receiving radio frequency signals from the patient receiving region;

a pulse oximeter including:

a pulse oximetry sensor unit for sensing patient pulse and blood oxygen characteristics and generating electrical signals indicative thereof on a connected electrical lead disposed in the bore liner;

a preamplifier grounded to the magnet assembly and surrounded by a shield connected with the magnet assembly, the preamplifier being connected with the sensor unit electrical lead for amplifying the electrical signals from the sensor unit;

a processing and display means connected with the preamplifier for processing the amplified electrical signals therefrom to generate a display indicative of at least patient pulse and blood oxygen concentration.

13. The apparatus as set forth in claim 12 further including a filter means disposed between the sensor unit and the preamplifier for blocking the passage of resonance frequency signals.

14. The apparatus as set forth in claim 12 further including a low pass filter mounted inside the shield with the preamplifier for blocking the passage of radio frequency signals from the preamplifier to the processing and display means.

15. The apparatus as set forth in claim 14 wherein the processing and display means includes a clock generator which generates a radio frequency signal, the resonance frequency and the radio frequency signal being harmonics of each other.

16. The apparatus as set forth in claim 15 further including a radio frequency filter connected between the preamplifier with the processing and control means and connected with a shielded room which surrounds the magnet assembly and is disposed between the preamplifier and the processing and control means.

17. The apparatus as set forth in claim 12 further including a plug on the sensor unit lead and a socket mounted in the bore liner, the socket being connected with the preamplifier.

18. A combined magnetic resonance and pulse oximetry sensing apparatus comprising:

a bore liner for defining a patient receiving region;

a magnetic resonance means for inducing magnetic resonance in and receiving magnetic resonance signals from at least a selected region of a patient disposed within the bore liner;

a socket mounted in the bore liner detachably receiving a plug on the end of a lead connected with a pulse oximetry sensor unit;

a preamplifier connected with the socket for amplifying electrical signals from the sensor unit;

a processing and display means connected with the preamplifier for processing electrical signals therefrom to generate a display of at least patient blood oxygen concentration.

19. The apparatus as set forth in claim 18 further including a filter means disposed between the socket and the preamplifier for blocking the passage of resonance frequency signals.

20. The apparatus as set forth in claim 18 wherein the preamplifier is grounded to the magnet assembly and surrounded by a shield connected with the magnet assembly.

* * * * *